US012754116B2

(12) United States Patent
Jogia et al.

(10) Patent No.: US 12,754,116 B2
(45) Date of Patent: Oct. 6, 2026

(54) BIORELEVANT DISSOLUTION MEDIA

(71) Applicant: Janssen Pharmaceutica NV, Beerse (BE)

(72) Inventors: Hitesh Jogia, Mumbai (IN); Bhavik Kansara, Mumbai (IN)

(73) Assignee: Janssen Pharmaceutica NV, Beerse (BE)

( * ) Notice: Subject to any disclaimer, the term of this patent is extended or adjusted under 35 U.S.C. 154(b) by 1216 days.

(21) Appl. No.: 17/621,377

(22) PCT Filed: Jun. 25, 2020

(86) PCT No.: PCT/EP2020/067902
§ 371 (c)(1),
(2) Date: Dec. 21, 2021

(87) PCT Pub. No.: WO2020/260499
PCT Pub. Date: Dec. 30, 2020

(65) Prior Publication Data

US 2022/0373446 A1 Nov. 24, 2022

(30) Foreign Application Priority Data

Jun. 28, 2019 (IN) ............................. 201911025939

(51) Int. Cl.
*G01N 13/00* (2006.01)
*G01N 33/15* (2006.01)

(52) U.S. Cl.
CPC ............. *G01N 13/00* (2013.01); *G01N 33/15* (2013.01); *G01N 2013/006* (2013.01)

(58) Field of Classification Search
CPC .. G01N 13/00; G01N 33/15; G01N 2013/006; G01N 23/02; G01N 23/20; G01N 2223/03; G01N 2223/102; G01N 2223/418
See application file for complete search history.

(56) References Cited

U.S. PATENT DOCUMENTS

2004/0115837 A1 6/2004 Schapaugh et al.
2005/0221501 A1 10/2005 Arnot et al.
2009/0145248 A1 6/2009 Leigh et al.

FOREIGN PATENT DOCUMENTS

WO 2004/051263 A1 6/2004
WO 2005/062041 A1 7/2005
WO 2007/054342 A1 5/2007

OTHER PUBLICATIONS

Fuchs et al., European Journal of Pharmaceuticals and Biopharmaceutics, 2015, 94, 229-240.
Galia et al., Pharmaceutical Research, 1998, vol. 15, No. 5.
Jantratid et al., Pharmaceutical Research, "Dissolution Media Simulating Conditions in the Proximal Human Gastrointestinal Tract: An Update", Jul. 2008, vol. 25, No. 7, 1663-1676.
Jogia, H., et al., "Evaluation of Dissolution Media Containing a Novel Synthetic Surfactant by In Vitro Testing of BCS Class II Drugs," Dissolution Technologies, vol. 16, No. 3, Aug. 26, 2009, pp. 14-19.
Xie et al., European Journal of Pharmaceuticals and Biopharmaceutics, 88, 2014, 565-573.
"Information for the package leaflet regarding 4 polysorbates used as excipients in medicinal products for 5 human use," European Medicines Agency, Committee for Medicinal Products for Human Use (CHMP), Nov. 19, 2018.
Bouwstra, "Prenatal and early postnatal long-chain polyunsaturated fatty acid status : do they affect neurodevelopmental outcome in healthy term infants?" Amsterdam University Medical Center, Jul. 30, 1980.

*Primary Examiner* — Snigdha Maewall
(74) *Attorney, Agent, or Firm* — BakerHostetler

(57) ABSTRACT

Herein disclosed are biorelevant dissolution media using a phosphonocholic acid salt in combination with a polysorbate. This tailor-made combination of surface-active agents apparently forms mixed micelles similar to those formed in the currently available biorelevant media, is faster and easier to prepare, forms reproducible and consistent dissolution media, and compares well with the predictive properties of currently available biorelevant dissolution media and thus is useful to predict the in vivo behavior of dosage forms of poorly water-soluble drugs.

18 Claims, 7 Drawing Sheets

BIORELEVANT DISSOLUTION MEDIA

CROSS-REFERENCE TO RELATED APPLICATIONS

This application is the National Stage of International Patent Application No. PCT/EP2020/067902, filed Jun. 25, 2020, which claims priority to Indian Patent Application number 201911025939, filed Jun. 28, 2019. The foregoing applications are incorporated herein by reference in their entireties for any and all purposes.

FIELD OF THE INVENTION

Herein disclosed are biorelevant dissolution media using a phosphonocholic acid salt in combination with a polysorbate. This tailor-made combination of surface-active agents apparently forms mixed micelles similar to those formed in currently available biorelevant media, is faster and easier to prepare, forms reproducible and consistent dissolution media, and compares well with the predictive properties of currently available biorelevant dissolution media and thus is useful to predict the in vivo behavior of dosage forms of poorly water-soluble drugs.

BACKGROUND OF THE INVENTION

Biorelevant dissolution media are a pivotal analytical tool to assess in vivo pharmacokinetics of drug products. The current classical biorelevant media contain natural bile acids such as sodium taurocholate (NaTC) as primary surfactant along with natural lecithin as secondary lipophilic surfactant. Bile acids have a planar structure comprising hydrophilic hydroxyl groups on the α (alpha) face while hydrophobic methyl groups project from the β (beta) face. Lecithin which is a water-insoluble amphipathic surfactant that forms mixed micelles (European Journal of Pharmaceutics and Biopharmaceutics 88 (2014) 565-573) with bile salts in aqueous media. These mixed micelles are capable of solubilizing poorly water-soluble drugs in a manner resembling gastrointestinal fluids and thus reproduce in vivo conditions. Solubilization of drugs by mixed micelles present in biorelevant media is different from solubilization by micelles comprising synthetic surfactants such as sodium laureth sulfate (SLS) and cetyl trimethyl ammonium bromide (CTAB). Their different micellar structures generally lead to differences in solubilizing properties. Current biorelevant media use expensive raw materials from a variety of natural sources, require a long, complex preparation (overnight stirring), and have a short optical and physical stability (1 day). The differences in the natural sources and extraction processes of both lecithin and sodium taurocholate result in variations in the purity and can lead to variations in the drug dissolution results.

During development of a drug product, in vitro dissolution testing in biorelevant media is of importance in assessing the probable in vivo performance of the potential formulations. The Fasted and Fed State Simulated Intestinal Fluids FaSSIF & FeSSIF were first described by Galia E. et al. in Pharmaceutical Research Vol. 15, No. 5, 1998 and have been modified a couple of times as FaSSIF V2 & FeSSIF V2 (Jantratid, E. et al. Pharmaceutical Research, Vol. 25, No. 7, July 2008) and FaSSIF V3 (Fuchs A., et al. European Journal of Pharmaceutics and Biopharmaceutics 94 (2015), 229-240).

Solid lyophilized powder containing a mixture of natural bile salt and lecithin is commercially available, which decreases the preparation time of biorelevant media. However, micelle aggregation, hydrolysis, lipid oxidation and microbial growth are some of the factors limiting the optical clarity and stability of these currently available biorelevant media.

Given that biorelevant media are an important tool during product development and have their limitations, several attempts have been made to simplify biorelevant media by replacing natural surfactants with synthetic surfactants such as SLS and polysorbates. It was found that none of these synthetic surfactants formed micelles which are similar in structure to intestinal micelles or micelles of available biorelevant medium, and as a result frequently lead to different rankings in dissolution profiles when e.g. comparing different formulations of a certain drug.

Dissolution media containing only 24-phosphonocholic acid are known from Jogia H; et al. Dissolution Technologies, 14-19 Aug. 2009, but absent a hydrophobic component such as lecithin may not adequately mimic human intestinal fluid and underestimate or overestimate in vivo dissolution, especially of poorly water-soluble drugs.

a—Novel simplified biorelevant fasted concept 1 medium;

b—Novel simplified biorelevant fasted concept 2 medium;

c—Novel simplified biorelevant fed concept 1 medium; and d—Novel simplified biorelevant fed concept 2 medium.

Figure 2:
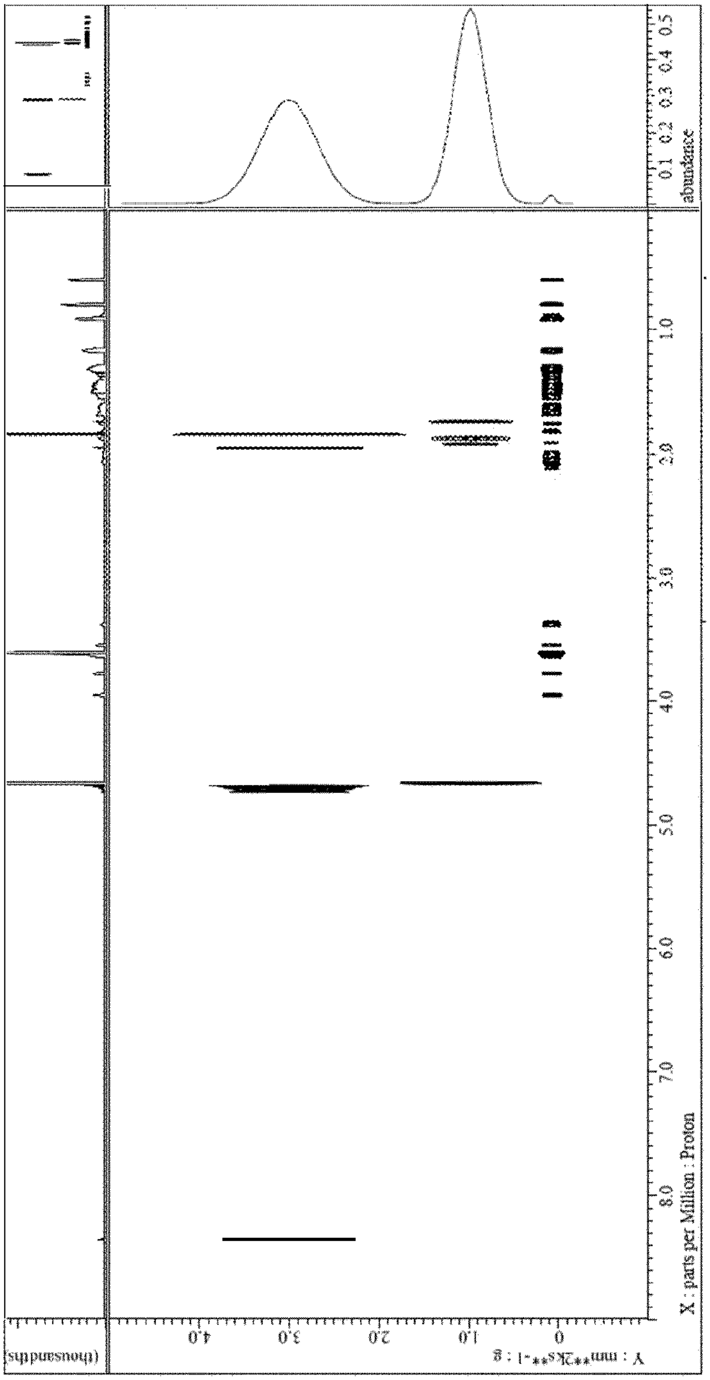

FIG. 2 is a DOSY NMR spectrum of a novel simplified biorelevant fed concept 2.

Figure 3:
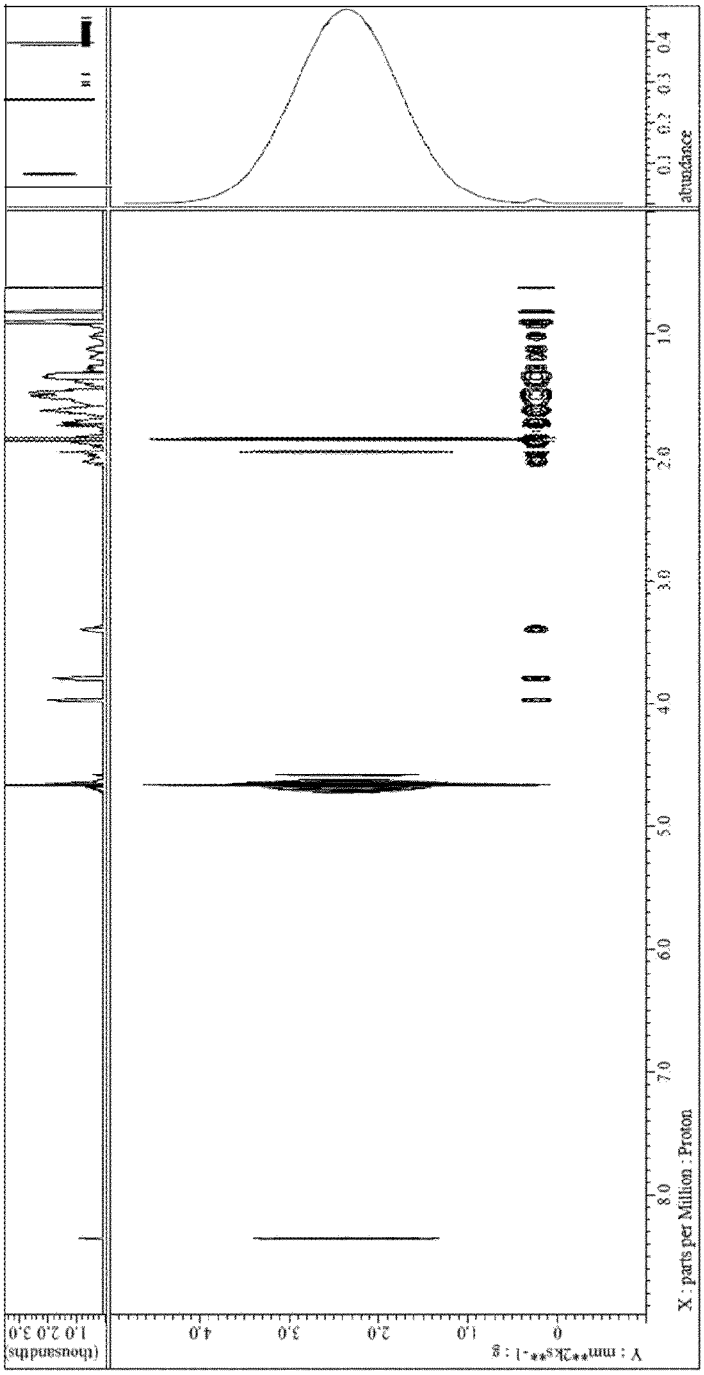

FIG. 3 is a DOSY NMR spectrum of medium only containing synthetic phosphonocholic acid disodium salt.

Figure 4:
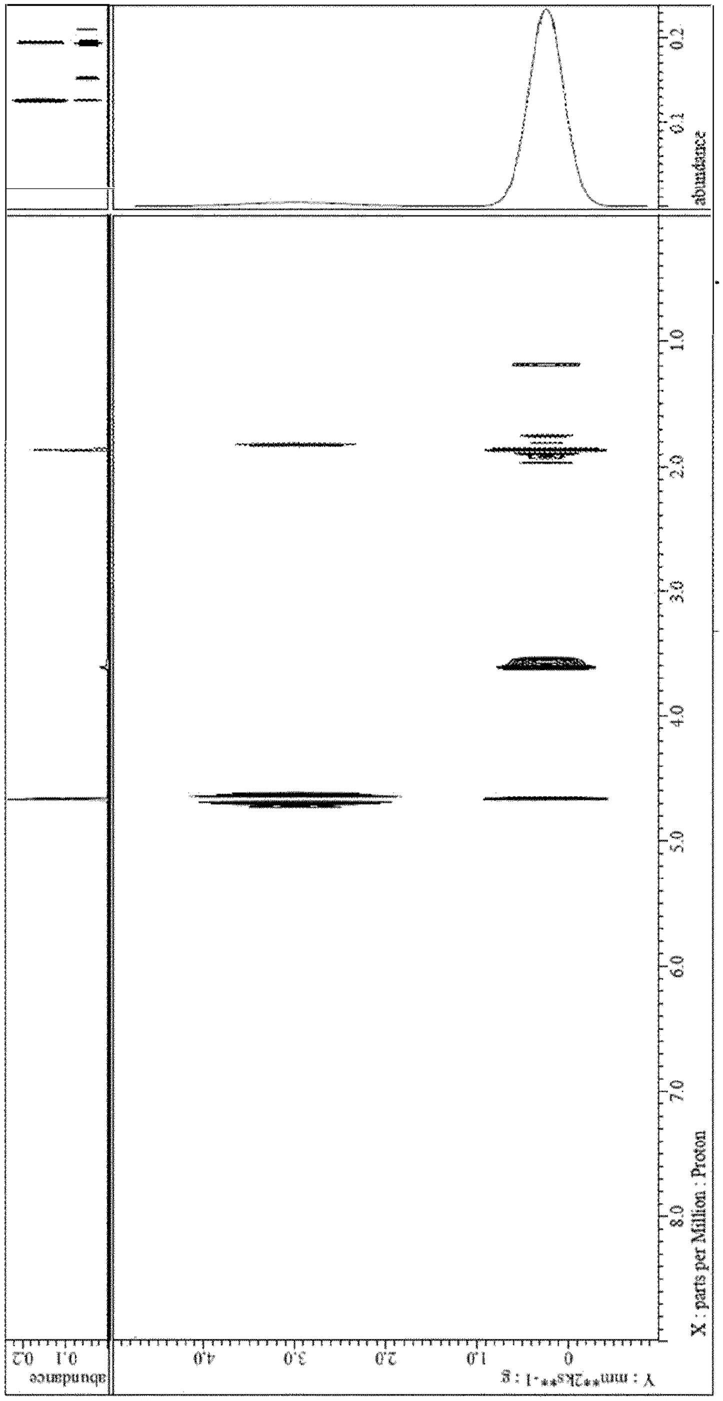

FIG. 4 is a DOSY NMR spectrum of medium only containing polysorbate.

Figure 5:
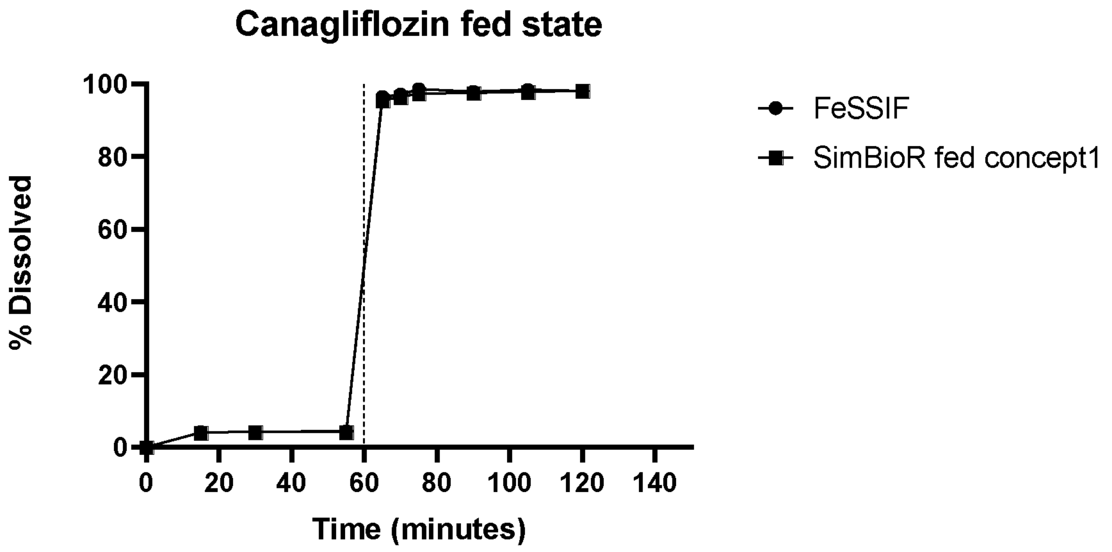

FIG. 5 shows two phase dissolution of canagliflozin 300 mg tablets in fed state intestinal medium.

Figure 6:
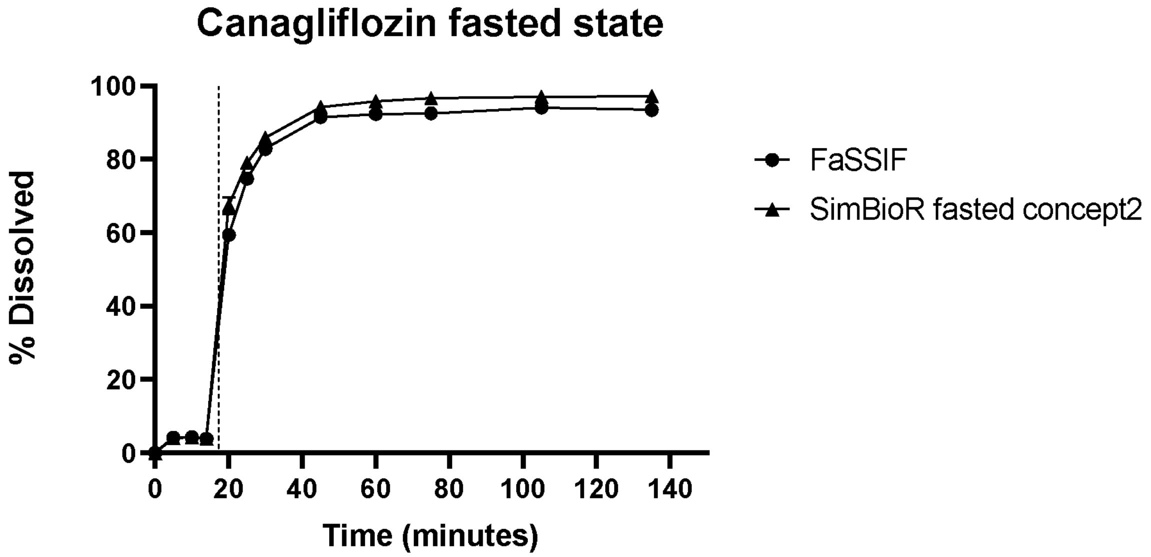

FIG. 6 shows two phase dissolution of canagliflozin 300 mg tablets in fasted state intestinal medium.

Figure 7:
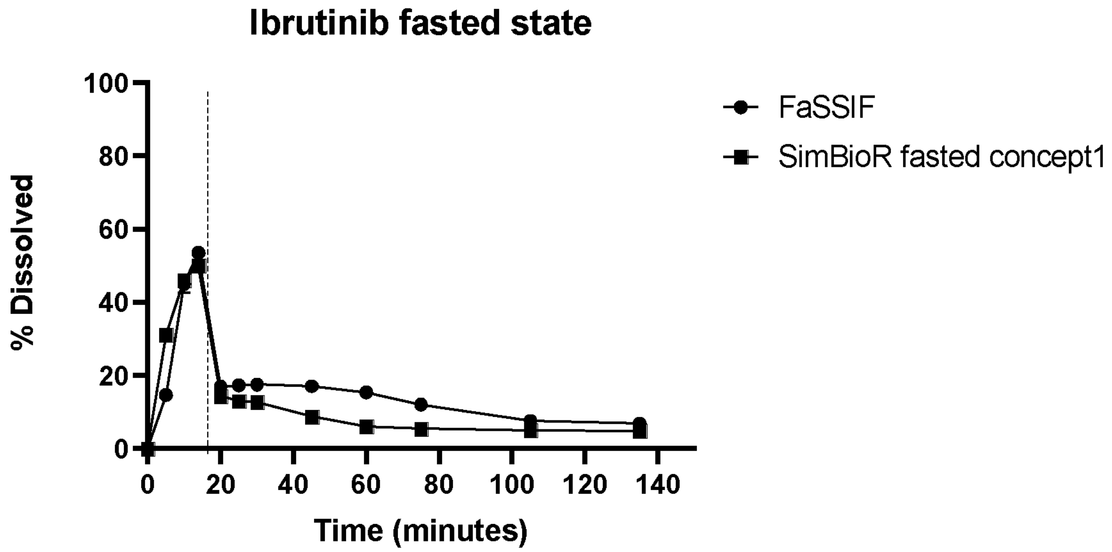

FIG. 7 shows two phase dissolution of ibrutinib 560 mg tablets in fasted state intestinal medium.

Figure 8:
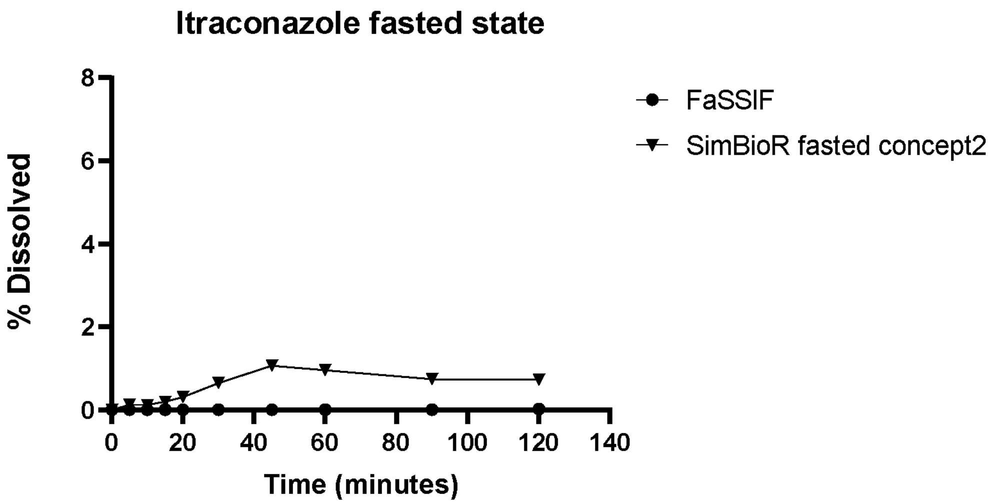

FIG. 8 shows the dissolution of itraconazole 100 mg capsules in fasted state intestinal medium.

Figure 9:
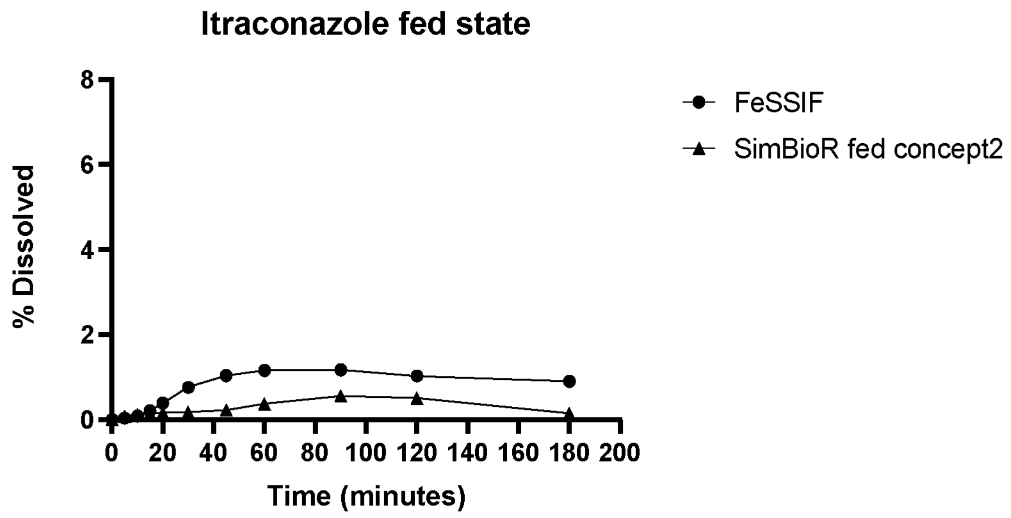

FIG. 9 shows the dissolution of itraconazole 100 mg capsules in fed state intestinal medium.

DETAILED DESCRIPTION OF THE INVENTION

We disclose novel simplified biorelevant media comprising a synthetic phosphonocholic acid salt in combination with a polysorbate. This medium is imitative of existing biorelevant dissolution medium with simple, rapid and reproducible preparation. The raw materials of the novel simplified biorelevant medium are synthetic, hence highest purity of raw material can be obtained, making novel simplified biorelevant medium more consistent compared to classical biorelevant media comprising natural ingredients. Novel simplified biorelevant media mimic the existing biorelevant dissolution media in fasted and fed gastrointestinal states, probably with similar solubilizing properties.

The synthetic phosphonocholic acids 1 (n=1; 23-phosphonocholic acid, 23-PCA or 3α,7α,12α-trihydroxy-24-nor-5β-cholane-23-phosphonic acid) and 2 (n=2; 24-phosphonocholic acid, 24-PCA or 3α,7α,12α-trihydroxy-5β-cholane-24-phosphonic acid) are known from Steroids 70 (2005) 681-689, have the core structure of natural bile salts, and tend to exhibit the same solubilization pattern (Scheme 1).

Polysorbates are polyoxyethylene 20 sorbitan mixtures of partial fatty acid esters (lauric, palmitic, stearic, oleic acid) and are hydrophilic non-ionic surfactants that can replace lecithin in simulated intestinal fluids.

The novel simplified biorelevant medium can be tailored to resemble the physiological properties of the gastrointestinal tract in fasted and fed conditions with respect to buffer capacity, surface tension, pH and osmolality.

It is an advantage of the presently disclosed dissolution media which comprise synthetic phosphonocholic acids and polysorbates in various concentration to provide dissolution media which mimic the classical biorelevant media. Another advantage is that the mixed micelles of the novel dissolution media behave in similar manner to that of biorelevant media. A major advantage of the novel dissolution media lies in the fact that they are simple to prepare compared to classical biorelevant media. In addition, they remain stable for a longer time (5 to 7 days). Moreover, the novel simplified biorelevant media comprise only synthetic surfactants of high purity making them consistently uniform resulting in more reproducible results. In addition, the novel simplified Scheme 1. Structural comparison of bile salts and lecithin with synthetic surfactant and polysorbate.

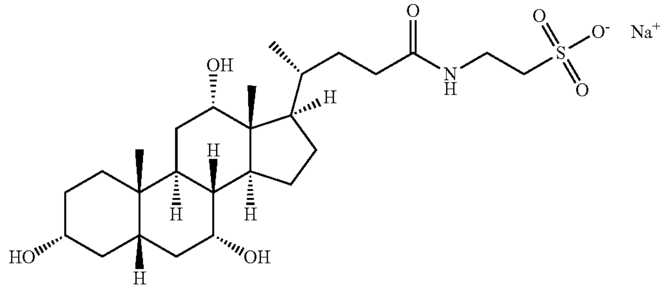

Sodium taurocholate

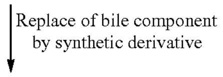

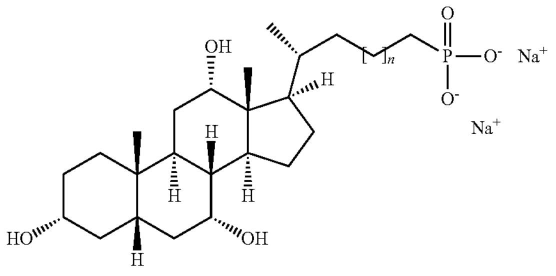

Synthetic phosphonocholic acid derivatev n = 1, 23-PCA
n = 2, 24-PCA

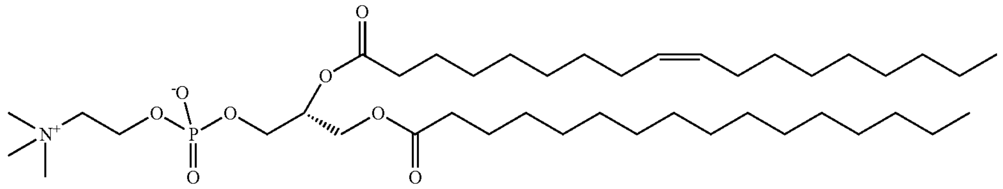

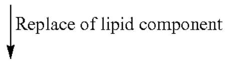

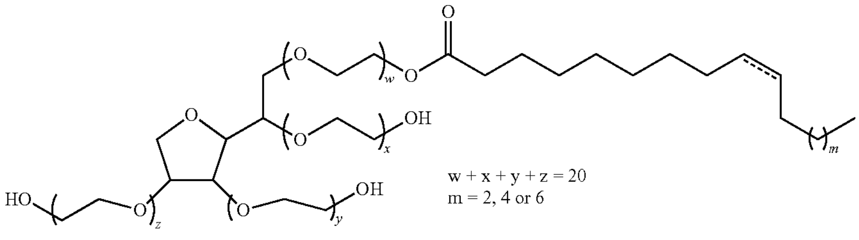

w + x + y + z = 20
m = 2, 4 or 6 biorelevant medium can be used as a physiologically relevant quality control and release testing medium in the supply chain. Another advantage of the invention is that novel simplified biorelevant media are optically clear with minimum background absorption allowing spectroscopic techniques to be used for detection and can be extended for use in automation and/or high-throughput techniques.

In certain embodiments of the media disclosed herein the biorelevant dissolution medium resembles gastrointestinal fluid and comprises a micellar solution comprising a synthetic phosphonocholic acid derivative, a polysorbate, buffer components and an osmotic agent; wherein the synthetic phosphonocholic acid derivative and the polysorbate have a mole ratio between about 1:1 and 20:1, in particular between about 3:2 and 15:1, more in particular between 2:1 and 6:1.

In certain embodiments of the media disclosed herein the medium simulates a fasted state intestinal fluid by adjustment of its pH to between about 6 and 7.

In certain embodiments of the media disclosed herein the medium simulating a fasted state intestinal fluid has an osmolality of less than 300 mOsmol/kg, in particular between 220 and 300 mOsmol/kg.

In certain embodiments of the media disclosed herein the medium simulates a fed state intestinal fluid by adjustment of its pH to about 4 to.

In certain embodiments of the media disclosed herein the medium simulating the fed state intestinal fluid has an osmolality of less than 700 mOsmol/kg, in particular between 600 and 700 mOsmol/kg.

In certain embodiments of the media disclosed herein the medium comprises polysorbate which is selected from the group of polysorbates consisting of polysorbate 20 (Polyoxyethylene 20 sorbitan monolaurate), polysorbate 80 (Polyoxyethylene 20 sorbitan monooleate), polysorbate 40 (Polyoxyethylene 20 sorbitan monopalmitate), polysorbate 60 (Polyoxyethylene 20 sorbitan monostearate), polysorbate 65 (Polyoxyethylene 20sorbitan tristearate), and polysorbate 85 (Polyoxyethylene 20 sorbitan trioleate).

In certain embodiments of the media disclosed herein the medium comprises sodium chloride as osmotic agent.

In certain embodiments of the media disclosed herein the medium comprises sodium dihydrogen phosphate as buffering agent and sodium chloride as osmotic agent.

In certain embodiments of the media disclosed herein the medium comprises the disodium salt of 23-phosphonocholic acid or 24-phosphonocholic acid.

In certain embodiments of the media disclosed herein the medium resembles human intestinal fluid in fasted conditions and comprises the ingredients

| | |
|---|---|
| a) disodium 24-phosphonocholic acid | 3 mM |
| b) polysorbate 80 | 0.75 mM |
| c) sodium dihydrogen phosphate | 3.95 g |
| d) sodium chloride | 6.18 g |
| e) sodium hydroxide | 0.35 g |
| f) water | qs ad 1 L. |

In certain embodiments of the media disclosed herein the medium resembles human intestinal fluid in fasted conditions and comprises the ingredients

| | |
|---|---|
| a) disodium 24-phosphonocholic acid | 3 mM |
| b) polysorbate 80 | 1.5 mM |
| c) sodium dihydrogen phosphate | 3.95 g |
| d) sodium chloride | 6.18 g |
| e) sodium hydroxide | 0.35 g |
| f) water | qs ad 1 L. |

-continued

In certain embodiments of the media disclosed herein the medium resembles human intestinal fluid in fed conditions and comprises the ingredients

| | |
|---|---|
| a) disodium 24-phosphonocholic acid | 15 mM |
| b) polysorbate 80 | 3.75 mM |
| c) acetic acid | 8.65 g |
| d) sodium chloride | 11.8 g |
| e) sodium hydroxide | 4.04 g |
| f) water | qs ad 1 L. |

In certain embodiments of the media disclosed herein the medium resembles human intestinal fluid in fed conditions and comprises the ingredients

| | |
|---|---|
| a) disodium 24-phosphonocholic acid | 15 mM |
| b) polysorbate 80 | 7.5 mM |
| c) acetic acid | 8.65 g |
| d) sodium chloride | 11.8 g |
| e) sodium hydroxide | 4.04 g |
| f) water | qs ad 1 L. |

In certain embodiments the media disclosed herein may be prepared by individually weighing and dissolving the ingredients in water.

In certain embodiments the media disclosed herein may be used for solubility testing, dissolution testing, drug release assessment, IVIVC, drug supersaturation, drug precipitation, and drug stability testing.

In certain embodiments of the media disclosed herein may be used in dissolution tests comprising adding a dosage form to a dissolution medium as defined hereinbefore and measuring at regular time intervals the concentration of the analyte or analytes of interest.

The impact of the concentration of lecithin on the solubilizing capacity of existing dissolution media is higher for poorly soluble drugs having higher log P value; thus, it is important to match the solubilization characteristics of lipophilic drugs in the novel simplified biorelevant media to those of classical biorelevant media. Lecithin was replaced with polysorbate in the novel simplified biorelevant media in two approaches considering solubilization capacity and lipophilicity of drug substance Two approaches were followed to replace lecithin with polysorbates:

1. Molar replacement—Replacement of lecithin in the novel simplified biorelevant media with equimolar amount of polysorbate (concept 1) which can be used for less lipophilic drugs.
2. Stoichiometric replacement of lipophilic character—Replacement of lecithin (having 2 Hydrocarbon chain) with 2 molar equivalents of polysorbates, so as to balance the lipophilic properties of the novel simplified biorelevant media with classical biorelevant media (concept 2).

The novel simplified biorelevant medium disclosed herein is intended to be used in single phase dissolution approaches to study how gastric or intestinal conditions impact on drug product release, as well as in two- or multiple-phase dissolution approaches mimicking the in vivo transit from gastric to intestinal conditions in one vessel to study the impact of gastric phase on drug product prior to intestinal impact.

Experimental Part

Physicochemical Characterization of Novel Simplified Biorelevant Medium

To attain highest degree of biorelevance to in vivo human intestinal fluids; a medium must possess values of pH, buffer capacity, osmolality, bile components, lipids components and surface tension close to those of human intestinal fluids. Various physicochemical properties of the novel simplified biorelevant medium were determined, where the medium was found to have similar values with that of the classical biorelevant medium and human intestinal fluids in fasted and fed conditions. The composition and physicochemical characteristics of the novel simplified biorelevant are depicted in table 1 and 2.

TABLE 1

| Proposed novel simplified biorelevant fasted state intestinal medium | | |
|---|---|---|
| Compound/Parameter (1 L) | fasted concept 1 | fasted concept 2 |
| Synthetic Phosphonocholic acid derivate | 3 mM | 3 mM |
| Polysorbate | 0.75 mM | 1.5 mM |
| Bile:Polysorbate Ratio | 4:1 | 2:1 |
| Sodium dihydrogen phosphate | 3.95 G | 3.95 G |
| Sodium chloride | 6.18 G | 6.18 G |
| Sodium hydroxide | 0.35 G | 0.35 G |
| pH | 6.5 | 6.5 |
| Surface Tension (mN/m) | 41.14 | 43.51 |
| Osmolarity (mOsmol/kg) | 263 | 262 |
| Buffer capacity | 9 mmol L−1 ΔpH −1 | 9 mmol L−1 ΔpH −1 |

TABLE 2

| Proposed novel simplified biorelevant fed state intestinal medium | | |
|---|---|---|
| Compound/Parameter (1 L) | fed concept 1 | fed concept 2 |
| Synthetic Phosphonocholic acid derivate | 15 mM | 15 mM |
| Polysorbate | 3.75 mM | 7.5 mM |
| Bile:Polysorbate | 4:1 | 2:1 |
| Acetic acid | 8.65 G | 8.65 G |
| Sodium chloride | 11.8 G | 11.8 G |
| Sodium hydroxide | 4.04 G | 4.04 G |
| pH | 5 | 5 |
| Surface Tension (mN/m) | 35 | 37 |
| Osmolarity (mOsmol/kg) | 661 | 662 |
| Buffer capacity | 78 mmol L−1 ΔpH −1 | 78 mmol L−1 ΔpH −1 |

Microscopic Characterization of Novel Simplified Biorelevant Medium

Figure 1:
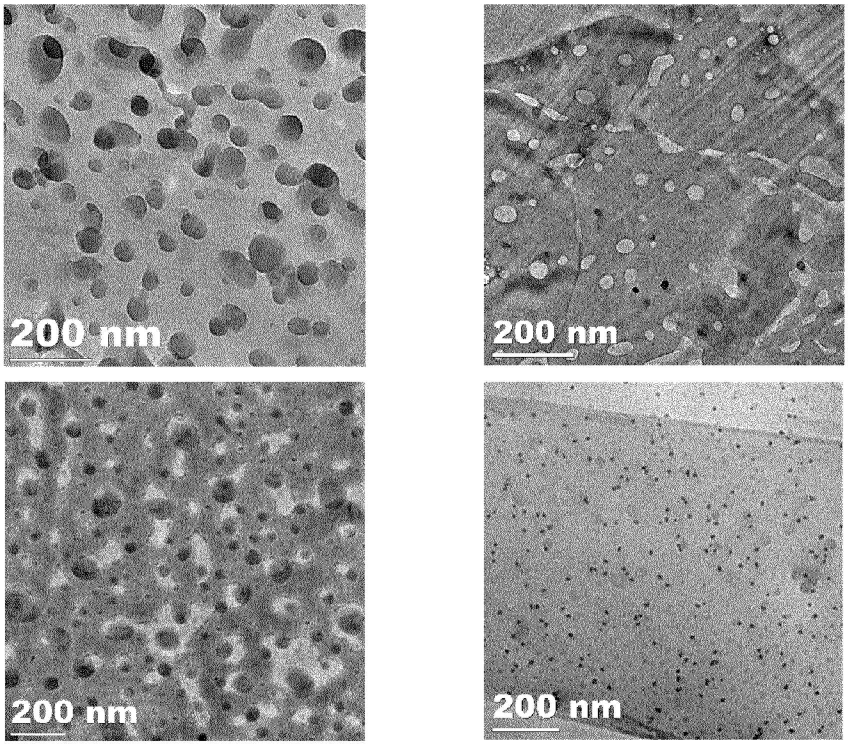
FIG. 1 shows Cryo-TEM microscopic images of dissolution media.

The microscopic characterization of the micellar structure in the novel simplified biorelevant medium was carried out using Cryo-transmission electron microscopy (Cryo-TEM), which is a useful tool to visualize and characterize colloidal particles. The Cryo-TEM images were obtained by rapid cooling of the sample, keeping the sample as close as possible to original condition and providing a clear view of the micellar nanostructures. The images were made using an Orius Gatan high resolution CCD camera. The images, which were taken at different magnifications, were analyzed using Gatan Digital Micrograph software. The main parameters studied were the particle size and micellar nanostructures. The Cryo-TEM image of the novel dissolution medium show presence of numerous round structures consistent with spherical micelles, all of which are of almost 100% spherical in shape with aspect ratio one, and almost 100% unilamellar as depicted in FIG. 1. The size of micelles formed in the medium ranged from 1 to 150 nm which is in line with the micelles found in the classical biorelevant media.

Characterization of Mixed Micelles in the Novel Simplified Biorelevant Medium by DOSY NMR DOSY (Diffusion Ordered Spectroscopy) is a technique which separates NMR signals in a mixture based on their differing diffusion coefficient which in turn is dependent on the shape and size of the molecule. The output from a DOSY experiment can be presented as a 2D map in which each spot is characterized by the $^1$H chemical shift and the diffusion coefficient of the respective molecule to determine the nature of the micelle/aggregate formed. DOSY NMR allowed simultaneous determination of molecular composition and micelle size, while shift of peak position in one-dimensional NMR spectra was used to investigate and confirm interactions between polysorbate and synthetic phosphonocholic acid derivative molecules inside the mixed micelle.

In brief, three different fed state dissolution media in deuterated water containing novel simplified biorelevant fed concept 2, synthetic phosphonocholic acid derivative alone and polysorbate alone were prepared, for the comparison and confirmation of mixed micelle. The fed condition was selected for assessment of mixed micelles, considering its higher concentration of surfactants. The DOSY NMR spectrum of these mediums are given in FIGS. 2, 3 and 4 respectively.

The horizontal cross sections through the DOSY spectrum of the Novel simplified biorelevant fed concept 2 (FIG. 2) at a diffusion constant of 0.07 $mm^2/ks$ shows an $^1$H-NMR spectrum that consists of the superposition two sets of signals. The signals between 3.7 and 4.0 ppm belong to the synthetic phosphonocholic acid derivative, whereas those between 3.5 and 3.7 ppm belong to polysorbate. This shows that synthetic phosphonocholic acid derivative and polysorbate are present in mixed micelle/aggregates.

Further evidence for the presence of mixed micelles in the novel simplified biorelevant fed concept 2 are confirmed from subtle differences observed between the chemical shifts of $^1$H-NMR signals in the various horizontal cross sections of the DOSY spectra. $^1$H-NMR chemical shifts of the signals in the cross section at 0.07 $mm^2/ks$ of the DOSY spectra of the novel simplified biorelevant fed concept 2 (FIG. 2) differ from those in the cross section at 0.23 $mm^2/ks$ of the DOSY spectra of the synthetic phosphonocholic acid derivative (FIG. 3). Also, the two signals between 0.95 and 1.05 ppm in the synthetic phosphonocholic acid derivative spectra, are missing in the novel simplified biorelevant fed concept 2 spectrum (FIG. 2). Similarly, the three different polysorbate related cross sections (at 1.7 $mm^2/ks$ of the DOSY spectra of polysorbate alone medium (FIG. 4) and at 0.98 and 0.07 mm2/ks of the DOSY spectra of the novel simplified biorelevant fed concept 2 (FIG. 3) show subtle but significant changes in $^1$H-NMR chemical shifts.

These changes in chemical shifts strongly suggest that the chemical environment of the synthetic phosphonocholic acid derivative and polysorbate molecules is different in the novel simplified biorelevant fed concept 2 medium as compared to the medium containing only synthetic phosphonocholic acid derivative and medium containing only polysorbate. This can only be explained if the synthetic phosphonocholic acid derivative and polysorbate molecules are in close contact in the novel simplified biorelevant fed concept 2 medium confirming formation of mixed micelles.

Dissolution Assessment of the Novel Simplified Biorelevant Media

The dissolution assessment of the novel simplified biorelevant medium was carried out on three poorly soluble drugs, of which two belonged to BCS class II and one to BCS class IV with lower and higher log P values. As they are poorly soluble, their solubility is driven by the mixed micelles present in the intestinal fluids. Thus, any similarity in the dissolution of such drugs translates to in vivo resemblance. Dissolution profiles of the said drugs were generated in the classical biorelevant medium and ion the novel simplified biorelevant medium concept 1 or 2 in fasted and fed conditions for head to head comparison.

Two approaches were used to assess the medium, out of which one was a two-phase dissolution approach and other was a single-phase approach. A two-phase dissolution approach simulates the transition of drug product from gastric to intestinal conditions within the same vessel. This approach helps to understand the impact of the gastric phase on the drug product prior to intestinal conditions. A single-phase approach is used when gastric and intestinal approaches are studied separately, in separate vessels.

Example 1. Canagliflozin is a neutral BCS class IV molecule, which in vivo shows a food effect. Dissolution was carried out in a two-phase setup in fed conditions. The purpose of this example was to compare the in vitro dissolution of immediate release oral tablets of canagliflozin (300 mg) in biphasic dissolution experiment consisting of gastric first phase of 300 mL 0.05 M phosphate buffer pH 4.9; followed by intestinal second phase of 900 mL of fed state of classical biorelevant medium and novel simplified biorelevant fed concept 1 medium pH 5. In the first phase, the tablets were stirred for 60 minutes at 75 rpm using a USP type II paddle apparatus, followed by 60 minutes in fed state medium (second phase). The results of this example demonstrate that the average dissolution profile in the novel simplified biorelevant fed concept 1 medium was matching that of FeSSIF medium. Dissolution profiles were rapid in both the media and sink condition was achieved in the novel simplified biorelevant concept 1 media, so further experiment with novel simplified biorelevant concept 2 was not performed. Sink condition means that the dissolution medium has the capacity to dissolve at least three times the amount of drug in the tested dosage form

TABLE 3

Average Dissolution Results of canagliflozin 300 mg tablets with a Paddle Apparatus at 75 rpm using two-phase, 300 ml phosphate buffer pH 4.9 media followed by fed state intestinal media 900 ml, pH 5 at 37° C. (N = 3)

| Time | Amount Dissolved (%) | | | | | |
|---|---|---|---|---|---|---|
| | FeSSIF | | | Novel simplified biorelevant fed concept1 | | |
| (min) | Avg | SD | RSD (%) | Avg | SD | RSD (%) |
| 15 | 4 | 0.08 | 2.04 | 4 | 0.07 | 1.71 |
| 30 | 4 | 0.03 | 0.65 | 4 | 0.02 | 0.47 |
| 55 | 4 | 0.18 | 4.13 | 4 | 0.06 | 1.35 |
| 65 | 96 | 1.20 | 1.25 | 95 | 1.06 | 1.11 |
| 70 | 97 | 1.16 | 1.19 | 96 | 0.79 | 0.82 |
| 75 | 99 | 0.69 | 0.70 | 97 | 0.23 | 0.24 |
| 90 | 98 | 0.81 | 0.83 | 98 | 0.29 | 0.30 |

TABLE 3-continued

Average Dissolution Results of canagliflozin 300 mg tablets with a Paddle Apparatus at 75 rpm using two-phase, 300 ml phosphate buffer pH 4.9 media followed by fed state intestinal media 900 ml, pH 5 at 37° C. (N = 3)

| Time | Amount Dissolved (%) | | | | | |
|---|---|---|---|---|---|---|
| | FeSSIF | | | Novel simplified biorelevant fed concept1 | | |
| (min) | Avg | SD | RSD (%) | Avg | SD | RSD (%) |
| 105 | 98 | 0.31 | 0.31 | 98 | 0.36 | 0.37 |
| 120 | 98 | 0.96 | 0.98 | 98 | 0.32 | 0.33 |

Avg = average;
SD = standard deviation;
RSD = relative standard deviation

Example 2. A two-phase dissolution approach was carried out for canagliflozin (300 mg) in fasted condition. Here the novel simplified biorelevant concept 2 media was selected as log P value is 5.34 and amount of lecithin has high impact on solubility of lipophilic drug. The experiment consisted of a first (gastric) phase using 300 ml SGF pH 1.3 followed by the second (intestinal) phase using 900 ml of fasted state intestinal medium pH 6.5. of FaSSIF and novel simplified biorelevant fasted concept 2 medium. The tablets were stirred at 75 rpm using a USP type II paddle apparatus for 15 minutes followed by 120 minutes in fasted state simulated intestinal medium. The results of this example also reveal similarity of novel simplified biorelevant media concept 2 to that of FaSSIF medium.

TABLE 4

Average Dissolution Results of canagliflozin 300 mg tablets with a Paddle Apparatus at 75 rpm using two-phase, 300 ml SGF pH 1.3 media followed by fasted state intestinal media 900 ml, pH 6.5 at 37° C. (N = 3)

| Time | Amount Dissolved (%) | | | | | |
|---|---|---|---|---|---|---|
| | FaSSIF | | | Novel simplified biorelevant fasted concept2 | | |
| (min) | Avg | SD | RSD(%) | Avg | SD | RSD (%) |
| 5 | 4 | 0.03 | 0.83 | 4 | 0.06 | 1.42 |
| 10 | 4 | 0.01 | 0.22 | 4 | 0.01 | 0.23 |
| 14 | 4 | 0.00 | 0.11 | 4 | 0.18 | 4.35 |
| 20 | 59 | 0.17 | 0.28 | 67 | 2.21 | 3.29 |
| 25 | 75 | 0.09 | 0.12 | 79 | 0.58 | 0.73 |
| 30 | 83 | 0.40 | 0.48 | 86 | 0.38 | 0.45 |
| 45 | 91 | 0.68 | 0.75 | 94 | 0.52 | 0.56 |
| 60 | 92 | 0.71 | 0.77 | 96 | 0.48 | 0.50 |
| 75 | 93 | 1.16 | 1.25 | 97 | 0.67 | 0.69 |
| 105 | 94 | 0.79 | 0.84 | 97 | 0.87 | 0.90 |
| 135 | 93 | 0.13 | 0.14 | 97 | 0.50 | 0.52 |

Avg = average;
SD = standard deviation;
RSD = relative standard deviation

Example 3. Ibrutinib is an alkaline drug that has a high solubility in acidic gastric medium. Due to its low solubility in a higher pH, it potentially can precipitate in the intestinal fluids. The purpose of this example was to compare the in vitro dissolution of immediate release oral tablets of ibrutinib (560 mg) in a two-phase dissolution experiment consisting of a first gastric phase of 300 mL SGF pH 1.3; followed by intestinal fasted state 900 mL FaSSIF or novel simplified biorelevant fasted concept 1 media at pH 6.5. Tablets were stirred for 15 minutes using a USP type II paddle apparatus 75 rpm, followed by 120 minutes in fasted state simulated intestinal medium. The precipitation observed in the dissolution profile obtained in the novel simplified biorelevant fasted concept 1 media matches that observed in FaSSIF. Ibrutinib has log P value of 3.94, making it less lipophilic, hence novel simplified biorelevant fasted concept 1 media was used to compare performance with classical FaSSIF. Novel simplified biorelevant fasted concept 1 dissolution profile of Ibrutinib tablets matches with classical FaSSIF media.

TABLE 5

Average Dissolution Results of ibrutinib 560 mg tablets with a Paddle Apparatus at 75 rpm using two-phase, 300 ml SGF pH 1.3 media followed by fasted state intestinal media 900 ml, pH 6.5 at 37° C. (N = 3)

| Time | Amount Dissolved (%) | | | | | |
|---|---|---|---|---|---|---|
| | FaSSIF | | | Novel simplified biorelevant fasted concept1 | | |
| (min) | Avg | SD | RSD (%) | Avg | SD | RSD (%) |
| 5 | 15 | 1.13 | 7.72 | 31 | 0.52 | 1.66 |
| 10 | 45 | 2.38 | 5.29 | 46 | 0.63 | 1.36 |
| 14 | 54 | 1.45 | 2.71 | 50 | 0.32 | 0.64 |
| 20 | 17 | 0.25 | 1.48 | 14 | 1.12 | 7.75 |
| 25 | 17 | 0.30 | 1.74 | 13 | 0.27 | 2.10 |
| 30 | 18 | 0.21 | 1.17 | 13 | 0.66 | 5.16 |
| 45 | 17 | 0.48 | 2.78 | 9 | 1.72 | 19.48 |
| 60 | 15 | 0.49 | 3.16 | 6 | 0.46 | 7.61 |
| 75 | 12 | 0.40 | 3.28 | 5 | 0.18 | 3.25 |
| 105 | 8 | 0.15 | 2.04 | 5 | 0.09 | 1.84 |
| 135 | 7 | 0.04 | 0.53 | 5 | 0.01 | 0.17 |

Avg = average;
SD = standard deviation;
RSD = relative standard deviation

Example 4. Itraconazole is a poorly soluble drug with log P of 6.5; with low solubility in the intestinal tract. To simulate the solubilization characteristics of itraconazole (highly lipophic drug) a dissolution was performed in novel simplified biorelevant simulating fasted and fed condition concept 2 media. The example serves to depict the low solubility of itraconazole in classical biorelevant media, which is also observed in the novel simplified biorelevant media. The purpose of this example was to compare the in vitro dissolution of oral capsules of itraconazole (100 mg) in a single-phase dissolution experiment consisting of 500 ml of fasted state simulated intestinal medium FaSSIF and novel simplified biorelevant fasted concept 2 medium at pH 6.5 and 500 ml fed state simulated intestinal medium, FeSSIF and novel simplified biorelevant fed concept 2 medium at pH 5. Briefly the capsules were stirred at 75 rpm using a USP type II paddle apparatus in a dissolution vessel for 120 minutes for the fasted state and 180 minutes for the fed state. The example shows that novel simplified biorelevant concept 2 medium does not overestimate the dissolution profile of poorly soluble drug and behaves similar to classical biorelevant media.

TABLE 6

Average Dissolution Results of itraconazole 100 mg capsules with a Paddle Apparatus at 75 rpm, 500 ml fasted state intestinal media pH 6.5 at 37° C. (N = 3)

| Time | Amount Dissolved (%) | | | | | |
|---|---|---|---|---|---|---|
| | FaSSIF | | | Novel simplified biorelevant concept2 | | |
| (min) | Avg | SD | RSD (%) | Avg | SD | RSD (%) |
| 5 | 0 | 0.00 | 173.21 | 0 | 0.08 | 173.21 |
| 10 | 0 | 0.00 | 173.21 | 0 | 0.01 | 173.21 |

TABLE 6-continued

Average Dissolution Results of itraconazole 100 mg capsules with a Paddle Apparatus at 75 rpm, 500 ml fasted state intestinal media pH 6.5 at 37° C. (N = 3)

| Time | Amount Dissolved (%) | | | | | |
|---|---|---|---|---|---|---|
| | FaSSIF | | | Novel simplified biorelevant concept2 | | |
| (min) | Avg | SD | RSD (%) | Avg | SD | RSD (%) |
| 15 | 0 | 0.01 | 65.30 | 0 | 0.01 | 65.30 |
| 20 | 0 | 0.00 | 76.04 | 0 | 0.03 | 76.04 |
| 30 | 0 | 0.01 | 72.61 | 1 | 0.07 | 72.61 |
| 45 | 0 | 0.00 | 14.91 | 1 | 0.12 | 14.91 |
| 60 | 0 | 0.00 | 41.29 | 1 | 0.05 | 41.29 |
| 90 | 0 | 0.00 | 38.56 | 1 | 0.08 | 38.56 |
| 120 | 0 | 0.01 | 26.77 | 1 | 0.20 | 26.77 |

Avg = average;
SD = standard deviation;
RSD = relative standard deviation

TABLE 7

Average Dissolution Results of itraconazole 100 mg capsules with a Paddle Apparatus at 75 rpm, 500 ml fed state intestinal media pH 5 at 37° C. (N = 3)

| Time | Amount Dissolved (%) | | | | | |
|---|---|---|---|---|---|---|
| | FeSSIF | | | Novel simplified biorelevant fed concept2 | | |
| (min) | Avg | SD | RSD (%) | Avg | SD | RSD (%) |
| 5 | 0 | 0.00 | 9.18 | 0 | 0.07 | 10.62 |
| 10 | 0 | 0.00 | 2.15 | 0 | 0.01 | 3.19 |
| 15 | 0 | 0.01 | 6.00 | 0 | 0.01 | 20.68 |
| 20 | 0 | 0.01 | 3.64 | 0 | 0.02 | 17.31 |
| 30 | 1 | 0.09 | 11.61 | 0 | 0.03 | 18.54 |
| 45 | 1 | 0.03 | 3.12 | 0 | 0.06 | 56.52 |
| 60 | 1 | 0.05 | 4.53 | 0 | 0.13 | 75.28 |
| 90 | 1 | 0.06 | 5.00 | 1 | 0.04 | 76.71 |
| 120 | 1 | 0.11 | 10.82 | 1 | 0.07 | 88.13 |
| 180 | 1 | 0.03 | 3.38 | 0 | 0.01 | 12.62 |

Avg = average;
SD = standard deviation;
RSD = relative standard deviation

The above examples show that the novel simplified biorelevant fasted state media and novel simplified biorelevant fed state media mimics the dissolution profiles of selected poorly soluble drugs in existing fasted and fed state biorelevant medium.

The invention claimed is:

1. A biorelevant dissolution medium, comprising a micellar solution comprising a phosphonocholic acid salt that is a disodium salt of 23-phosphonocholic acid or of 24-phosphonocholic acid, a polysorbate, a buffer component and an osmotic agent; wherein the synthetic phosphonocholic acid salt and the polysorbate have a mole ratio between about 1:1 and 20:1.

2. The medium of claim 1 simulating a fasted state intestinal fluid by adjustment of its pH to between about 6 and 7.

3. The medium of claim 2 having an osmolality less than 300 mOsmol/kg.

4. The medium of claim 1 simulating a fed state intestinal fluid by adjustment of its pH to about 4 to 6.

5. The medium of claim 4 having an osmolality less than 700 mOsmol/kg.

6. The medium of claim 1, wherein the polysorbate is polysorbate 20 (Polyoxyethylene 20 sorbitan monolaurate), polysorbate 80 (Polyoxyethylene 20 sorbitan monooleate), polysorbate 40 (Polyoxyethylene 20 sorbitan monopalmitate), polysorbate 60 (Polyoxyethylene 20 sorbitan monostearate), polysorbate 65 (Polyoxyethylene 20 sorbitan tristearate), or polysorbate 85 (Polyoxyethylene 20 sorbitan trioleate).

7. The medium of claim 1, wherein the osmotic agent is sodium chloride.

8. The medium of claim 1, wherein the buffer component is sodium dihydrogen phosphate and the osmotic agent is sodium chloride.

9. The medium according to claim 1 comprising

| | |
|---|---|
| a) disodium 24-phosphonocholic acid | 3 mM |
| b) polysorbate 80 | 0.75 mM |
| c) sodium dihydrogen phosphate | 3.95 g |
| d) sodium chloride | 6.18 g |
| e) sodium hydroxide | 0.35 g |
| f) water | qs ad 1 L. |

10. The medium according to claim 1 comprising

| | |
|---|---|
| a) disodium 24-phosphonocholic acid | 3 mM |
| b) polysorbate 80 | 1.5 mM |
| c) sodium dihydrogen phosphate | 3.95 g |
| d) sodium chloride | 6.18 g |
| e) sodium hydroxide | 0.35 g |
| f) water | qs ad 1 L. |

11. The medium according to claim 1 comprising

| | |
|---|---|
| a) disodium 24-phosphonocholic acid | 15 mM |
| b) polysorbate 80 | 3.75 mM |
| c) acetic acid | 8.65 g |
| d) sodium chloride | 11.8 g |
| e) sodium hydroxide | 4.04 g |
| f) water | qs ad 1 L. |

12. The medium according to claim 1 comprising

| | |
|---|---|
| a) disodium 24-phosphonocholic acid | 15 mM |
| b) polysorbate 80 | 7.5 mM |
| c) acetic acid | 8.65 g |
| d) sodium chloride | 11.8 g |
| e) sodium hydroxide | 4.04 g |
| f) water | qs ad 1 L. |

13. The medium of claim 1, wherein the mole ratio is between about 3:2 and 15:1.

14. The medium of claim 1, wherein the mole ratio is 2:1 to 6:1.

15. The medium according to claim 1, wherein the medium resembles human intestinal fluid in fasted conditions.

16. The medium according to claim 1, wherein the medium resembles human intestinal fluid in fed conditions.

17. A method for preparing a medium of claim 1, comprising individually weighing and dissolving the phosphonocholic acid salt, polysorbate, buffer components and osmotic agent in water.

18. A dissolution test comprising adding a dosage form to a dissolution medium of claim 9 and measuring at regular time intervals the concentration of an analyte or analytes of interest.

* * * * *